United States Patent [19]

Banton et al.

[11] Patent Number: 6,028,092
[45] Date of Patent: Feb. 22, 2000

[54] SALTS OF N-(4-OXO-2-(1H-TETRAZOYL-5-YL)-4H-1-BENZOPYRAN-8-YL)-4-(4-PHENYLBUTOXY)BENZAMIDE

[75] Inventors: Christopher John Banton, Banstead; Phillip Christopher Buxton, Great Dunmow, both of United Kingdom

[73] Assignee: SmithKline Beecham p.l.c, Brentford, United Kingdom

[21] Appl. No.: 09/051,879

[22] PCT Filed: Oct. 18, 1996

[86] PCT No.: PCT/EP96/04650

§ 371 Date: Jun. 17, 1998

§ 102(e) Date: Jun. 17, 1998

[87] PCT Pub. No.: WO97/15569

PCT Pub. Date: May 1, 1997

[30] Foreign Application Priority Data

Oct. 20, 1995 [GB] United Kingdom .................... 9521490
Oct. 20, 1995 [GB] United Kingdom .................... 9521491

[51] Int. Cl.[7] .......................... A61K 31/35; A61K 31/41; C07D 257/04; C07D 405/04
[52] U.S. Cl. .......................... 514/382; 514/456; 514/460; 514/617; 514/622; 548/252; 548/253; 548/254; 549/401; 549/404; 549/407; 549/414; 564/161

[58] Field of Search .............................. 514/382; 548/252, 548/253, 254

[56] References Cited

FOREIGN PATENT DOCUMENTS 0173516 3/1986 European Pat. Off. .

OTHER PUBLICATIONS

Hackh's Chemistry Dictionary, Fourth Ed., Julius Grant, Ed., p. 249, 1969.

The Merck Index, Tenth Edition, Martha Windholz, Ed., pp. 207, 219, and 7439, 1983.

Aldrich, Catalog Handbook of Fine Chemicals, p. 1702, 1998–99.

*Primary Examiner*—Johann Richter
*Assistant Examiner*—Jane C. Osowecki
*Attorney, Agent, or Firm*—James M Kanagy; Charles M. Kinzig

[57] ABSTRACT

This invention relates to novel formulations of salts of certain benzopyran compounds, to compositions containing them and their use in the treatment of certain disorders.

8 Claims, No Drawings

SALTS OF N-(4-OXO-2-(1H-TETRAZOYL-5-YL)-4H-1-BENZOPYRAN-8-YL)-4-(4-PHENYLBUTOXY)BENZAMIDE

This application is a 371 of PCT/EP96/04650 filed Oct. 18, 1996.

This invention relates to novel formulations of compounds having pharmacological activity, to compositions containing them and to their use in the treatment of certain disorders.

N-[4-Oxo-2-(1H-tetrazol-5-yl)-4H-1-benzopyran-8-yl]-4-(4-phenylbutoxy)benzamide, that is to say, the compound of the following structure:

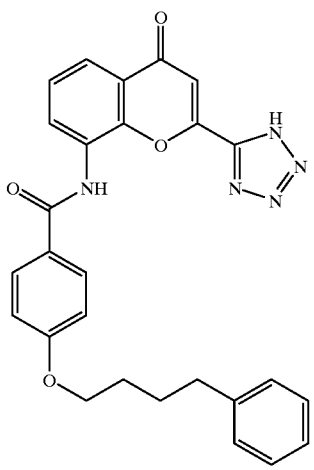

is known in the art as a compound which is useful as a leukotriene antagonist. In particular, the compound is disclosed in EPA 173 516 as being useful for the treatment of asthma. However this type of compound is relatively insoluble in many solvents commonly used in pharmaceutical formulations. This is clearly a disadvantage, since solubility can affect the bioavailability of any drug. There is therefore a need for novel formulations which overcome the above problems. It has been found that specific salts of the above compound are surprisingly soluble in certain organic solvents.

The present invention therefore provides, in a first aspect, a compound of formula (I):

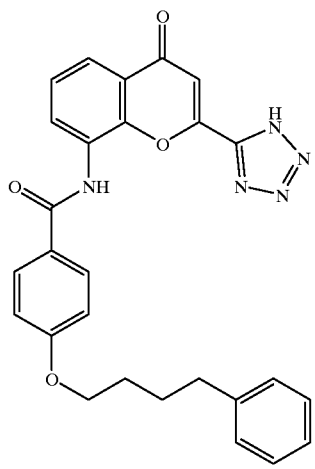

in the form of a salt characterised in that the salt is the sodium, potassium, ammonium calcium, Tris, triethanolamine, ethylenediamine or N-methyl glucamine salt.

Preferred inorganic salts include the sodium and ammonium salts.

These salts of the compound of formula (I) can be used in therapy, particularly for the treatment of asthma. Thus the invention also provides a salt as described herein, for use as a therapeutic substance, in particular for the treatment or prophylaxis of asthma.

Salts of the invention can be formulated in standard pharmaceutical compositions. The present invention therefore provides a pharmaceutical composition, which comprises a salt as described herein and a pharmaceutically acceptable carrier or mixture of carriers.

The salts of the invention show enhanced solubility in aqueous media when compared to the free acid. Therefore the carrier can be an aqueous based carrier. Advantageously, the salts of the invention can be formulated with one or more organic solvents, particularly solvents containing one or more hydroxy groups such as alcohol and glycol solvents. Preferred solvents include polyethylene glycols such as PEG 200 and PEG 400 as well as lower alcohols, in particular ethanol and n-propanol. Mixtures of two or more solvents can be used, including mixtures of alcohols or glycols in water. Particularly preferred compositions which exhibit excellent bioavailability are those containing the ammonium salt in PEG 400.

In a particular embodiment of the invention the salts of the invention can be formulated with polyethylene glycols at elevated temperature and the mixture then cooled and used to fill gelatin capsules.

Alternatively salts may be prepared in situ at the formulation stage from the parent compound of formula I and appropriate quantities of a neutralising base such as ammonium carbonate or sodium carbonate.

The invention further provides a method of treatment or prophylaxis of asthma, in mammals including humans, which comprises administering to the sufferer a therapeutically effective amount of a salt as described herein.

In another aspect, the invention provides the use of a salt as described herein in the manufacture of a medicament for the treatment or prophylaxis of the above disorders.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred, particularly capsules.

Compositions for oral administration may be in unit dose form, and may contain conventional excipients known in the pharmaceutical art.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a salt of the invention and a sterile vehicle. The salt, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 300 mg, more suitably 5 to 75.0 mg; and such unit doses may be administered more than once a day, for example two or three times a day.

The following Examples illustrate the invention.

In the experimental section below, the term "Compound I" refers to the compound of formula (I) mentioned herein, i.e. N-[4-Oxo-2-(1H-tetrazol-5-yl)-4H-1-benzopyran-8-yl]-4-(4-phenylbutoxy)benzamide Example 1

Preparation of Inorganic Salts

Compound 1 (10.0 g) was added to a stirred solution of anhydrous sodium acetate (1.7 g) in methanol (500 mL). The clear yellow solution obtained was reduced in volume by rotary evaporation to approximately 50 mL and the sodium salt allowed to crystallise. The damp mass was filtered and dried at 50° C. to give the sodium salt of Compound 1 (9.3 g).

The potassium and ammonium salts were prepared in a similar manner by using equimolar quantities of potassium and ammonium acetates. For the calcium salt the calcium acetate to Compound 1 molar ratio was 1:2.

Example 2

Preparation of Organic Salts

Compound 1 (10.0 g) was added to a stirred solution of N-methyl glucamine (4.0 g) in methanol (500 mL). The clear solution obtained was reduced to approximately 100 mL by rotary evaporation and the salt allowed to crystallise. The damp mass was filtered and dried at 50° C. to give the N-methyl glucamine salt of Compound 1 (7.6 g). A further 1.7 g of product was obtained by further concentration of the mother liquor.

The tris (hydroxymethyl) aminomethane, triethanolamine and ethylene diamine salts were prepared in a similar manner using equimolar quantities of each base except for the ethylene diamine salt where the base to Compound 1 molar ratio was 1:2.

Characterisation of Salts

The salts of Compound 1 were characterised by standard spectroscopic techniques and by measurement of physical parameters. A summary of representative physical properties is given in Table 1.

TABLE 1

Physical Properties of Compound 1 Salts

| Salt | Appearance | DSC | TGA | mp |
|---|---|---|---|---|
| Sodium | cream | 336° C. exotherm | 0.7% (wt. loss) 45° C.–110° C. | 290° C.–315° C. decompose |
| Potassium | cream | 290° C. exotherm | 4% (wt. loss) 30° C.–115° C. | 256° C.–270° C. decompose |
| Ammonium | cream | 242° C. exotherm | 8% (wt. loss) 92° C.–130° C. | 205° C.–234° C. decompose |
| Tris | cream | 99° C. exotherm | 4% (wt. loss) 68° C.–96° C. | 70° C.–95° C. |
| Triethanolamine | cream | 169° C. exotherm | 26% (wt. loss) 160° C.–280° C. | 145° C.–160° C. |
| Ethylenediamine | yellow | 134° C., 198° C. exotherm | 3% (wt. loss) 85° C.–128° C. | 184° C.–190° C. |

Example 3

Representative Solubility Data

TABLE 2

Solubility of Compound 1 Salts Expressed in g/l

| Salt | Solvent | | |
|---|---|---|---|
| | Water | Ethanol | PEG 400 |
| Sodium | 0.04 | >10 | >10 |
| Calcium | 0.00 | 0.36 | 8.42 |
| Ammonium | 0.28 | 9.33 | >10 |
| Meglumine | 0.34 | 3.06 | 9.20 |
| Triethanolamine | 0.33 | 3.91 | >10 |

The aqueous solubility of Compound 1 free acid is less than 0.01 g/l. The salts display an improved aqueous solubility but the improvement is limited. In contrast, the salts are significantly and unexpectedly more soluble in less polar solvents such as alcohols and ethers. The pharmaceutically relevant solvents ethanol and PEG 400 can yield salt solutions with concentrations greater than 10 g/l in certain cases (see table 2).

Example 4

In-situ Solubilisation

Although the salts of Compound 1 are freely soluble in solvents such as ethanol further improvements have been observed when the salts are prepared in situ.

TABLE 3

Solubility of Compound 1 in 50% Acetate Solution (0.1M) and 50% Ethanol

| Salt | Solubility |
|---|---|
| Potassium Acetate | 12.2 |
| Ammonium Acetate | 11.5 |
| Sodium Acetate | 11.0 |
| Calcium Acetate | 0.4 |

In the presence of excess acetate the salts formed in situ are freely soluble even in an aqueous alcoholic medium with a water content of 50%. With lower water contents or in the absence of water the solubility can be improved further. For example when PEG 200 (30 mL) sodium acetate (2.5 g) and Compound 1 (7.4 g) were triturated in a mortar and pestle the sodium salt of Compound 1 formed in-situ was solubilised to a concentration greater than 200 g/l.

The scope of in-situ solubilisation in terms of solvent type and buffer concentration can be seen in Table 4. In these experiments the sodium salt of Compound 1 was prepared through the presence of varying concentrations of sodium phosphate buffer solution with 50% of the test solvent.

TABLE 4

Solubility of Compound 1 in 50% solvent systems/50% sodium phosphate (pH7) at different molarities

| Solvent | Solubility (mg/mL) | | |
|---|---|---|---|
| Buffer Concentration | 0.1M | 0.25M | 0.5M |
| Methanol | 2.2 | 1.1 | 0.9 |
| Ethanol | 16.2 | N/T | N/T |
| n-Propanol | 18.0 | 43.1 | 56.3 |
| Propylene Glycol | 1.7 | 0.7 | 0.5 |
| Glycerol | 0.2 | 0.05 | 0.04 |
| PEG 400 | 20.5 | 23.7 | 26.6 |
| THF | 22.3 | 49.3 | 100.9 |
| Glycofurol | 19.5 | N/T | N/T |

N/T Not tested

No value was obtained for those N/T samples because the solvents were immiscible with the buffer solution at those concentrations.

Solubilities of organic salts of Compound 1 under similar conditions are summarised in Table 5.

TABLE 5

Solubility of Compound 1 in 50% 0.1M salt solution (pH7)/50% Absolute Alcohol

| Salt | Solubility (mg/mL) |
|---|---|
| Tris | 1.6 |
| Triethanolamine | 2.7 |
| Ethylenediamine | 1.7 |

The solubilities obtained are lower than those for the inorganic salts but can be improved significantly by increasing the pH of the solvent system.

Example 5

Sample Formulations

1. In situ Salt Formation during Formula Preparation

The parent acid of I (4.5 parts by weight) was triturated with anhydrous sodium acetate (1.8 parts by weight) in molten polyethylene glycol (50% by weight of PEG 4000 and PEG 400) sufficient to give a drug concentration of 150 mg/mL. The liquid is added in 1 mL aliquots into capsules and the contents allowed to set on cooling.

2. The ammonium or N-methylglucamine salts of Compound 1 were dissolved in PEG 400 sufficient to give an equivalent parent acid concentration of 5 g/l.

Example 6

Enhanced Bioavailability of Salt Forms

Following oral administration of a PEG 400 solution of the N-methylglucamine salt plasma concentrations of Compound 1 were variable but showed evidence of enhanced absorption with the absolute bioavailability increasing approximately fourfold relative to the parent acid. The absolute bioavailability increased approximately tenfold upon similar oral administration of a solution of the ammonium salt in PEG 400. The pharmacokinetic data (Table 6) indicated that the ammonium salt was reasonably well absorbed with an absolute bioavailability of approximately 7%.

TABLE 6

Mean ± SD pharmacokinetic parameters for Compound 1 in plasma following administration to rats

| Route | Compound | CMAX (ng/mL)[a] | TMAX (min) | THALF (min) | AUC)-t or ∞ (ug min/mL)[a] | BA (%) |
|---|---|---|---|---|---|---|
| IV | Compound 1 | — | — | 23.2 ± 28.4 | 171063.4 ± 26025.5 | — |
| oral susp | Free Acid | 207.4 ± 57.2 | 22.6 ± 14.9 | [b] | 36439.0 ± 7316.6 | 0.80 ± 0.16[c] |
| oral susp | Meglumine | 263.0 ± 139.5 | 97.5 ± 66.2 | [b] | 59012.7 ± 17096.3 | 1.29 ± 0.37[c] |
| oral susp | Ammonium | 264.5 ± 64.06 | 150.5 ± 34.1 | [b] | 66722.9 ± 16472.6 | 1.46 ± 0.36[c] |
| oral soln | Meglumine | 207.7 ± 112.2 | 53.1 ± 26.8 | [b] | 35290.4 ± 11719.1 | 3.09 ± 1.03[c] |
| oral soln | Ammonium | 548.5 ± 165.7 | 53.1 ± 29.8 | [b] | 81490.5 ± 23670.3 | 7.15 ± 2.08[c] |

[a]dose normalised to 3 mg/kg for IV, 80 mg/kg (acid eq.) for oral suspensions and 20 mg/kg (acid eq.) for oral solutions.
[b]insufficient points in the terminal portion of the profile to determine a terminal rate constant.
[c]bioavailability based on AUC)-t.

What is claimed is:

1. A pharmaceutical formulation comprising a salt of the compound of formula

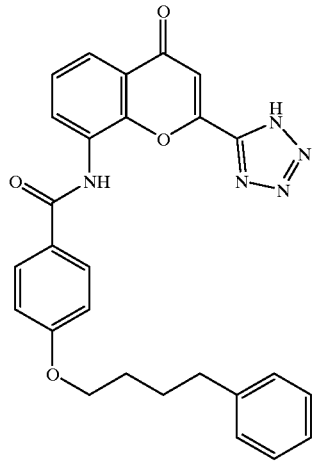

(I)

and a pharmaceutically acceptable carrier wherein the carrier is an organic solvent having one or more hydroxy groups and the salt form is sodium, potassium, ammonium calcium, tris(hydroxymethyl)aminomethane, triethanolamine, ethylenediamine, or N-methyl glucamine salt.

2. A formulation according to claim 1 in which the carrier is a lower alcohol.

3. A formulation according to claim 2 in which the carrier is ethanol or n-propanol.

4. A formulation according to claim 1 in which the carrier is a polyethylene glygol.

5. A method of treating asthma, which method comprises administering a pharamceutical formulation comprising a salt of the compound of formula (I)

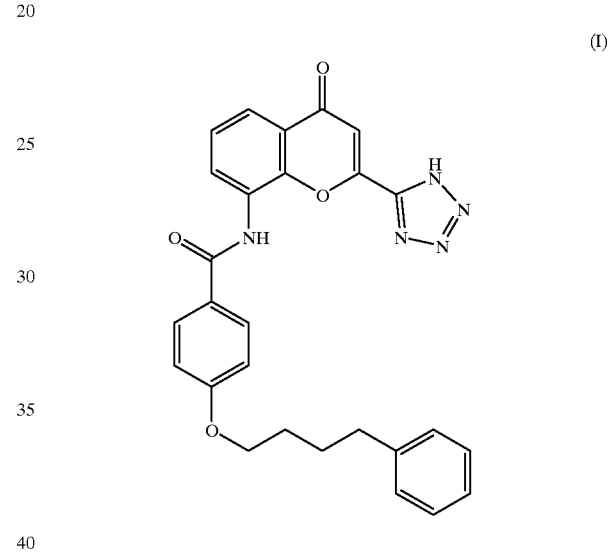

(I)

and a pharmaceutically acceptable carrier wherein the carrier is an organic solvent having one or more hydroxy groups and the salt form is sodium, potassium, ammonium calcium, tris(hydroxymethyl)aminomethane, triethanolamine, ethylenediamine, or N-methyl glucamine salt.

6. The method of claim 5 wherein, in the formulation, the carrier is a lower alcohol.

7. The method of claim 5 wherein, in the formulation, the carrier is ethanol or n-propanol.

8. The method of claim 5 wherein, in the formulation, the carrier is a polyethylene glygol.

* * * * *